United States Patent
Epps et al.

(10) Patent No.: US 6,582,907 B1
(45) Date of Patent: *Jun. 24, 2003

(54) USE OF FLUORESCENCE CORRELATION SPECTROSCOPY TO IDENTIFY COMPOUNDS THAT BIND TO TARGET SPECIES UNDER ISOTHERMAL DENATURING CONDITIONS

(75) Inventors: Dennis E. Epps, Portage, MI (US); Paul K. Tomich, Kalamazoo, MI (US); Ferenc J. Kezdy, Kalamazoo, MI (US); Charles K. Marschke, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/458,172

(22) Filed: Dec. 9, 1999

(51) Int. Cl.[7] .............................................. G01N 33/543

(52) U.S. Cl. ................. 435/6; 435/4; 435/7.1; 435/7.92; 435/23; 435/24; 436/501; 436/518; 436/536; 436/172; 436/537; 436/546; 436/55; 436/56; 436/147; 436/805

(58) Field of Search ........................... 435/4, 7.1, 7.92, 435/6, 23, 24; 436/501, 518, 536, 172, 537, 546, 55, 56, 147, 805

(56) References Cited

U.S. PATENT DOCUMENTS

| | | |
|---|---|---|
| 5,585,277 A | 12/1996 | Bowie et al. |
| 5,679,582 A | 10/1997 | Bowie et al. |
| 6,020,141 A | 2/2000 | Pantoliano et al. |
| 6,036,920 A | 3/2000 | Pantoliano et al. |
| 6,242,190 B1 | 6/2001 | Freire et al. |

FOREIGN PATENT DOCUMENTS

| | | |
|---|---|---|
| EP | 0 770 876 A | 5/1997 |
| WO | WO 97 20952 A | 6/1997 |
| WO | WO 97/42500 | 11/1997 |
| WO | WO 98/16814 | 4/1998 |
| WO | WO 99/29894 A | 6/1999 |

OTHER PUBLICATIONS

Maiti et al., A study of protein folding with two–photon fluorescence correlation spectroscopy, Biophysical Journal 70(2): part 2, A262 (Feb. 17–21, 1996).Abstract.*

Rigler, Fluorescence Correlations, single molecule detection and large number screening. Applications Biotechnology, Journal of Biotechnology 41(2-3): 177–186 (1995). Abstract.*

Blaber et al., Reversible themal denaturation of human FGF–1 induced by low concentration of guanidine hydrochloride, Biophysical Journal 77 (1): 470–477 (Jul., 1999) Abstract.*

(List continued on next page.)

Primary Examiner—Christopher L. Chin
Assistant Examiner—Gailene R. Gabel
(74) Attorney, Agent, or Firm—Mueting, Raasch & Gebhardt, P.A.

(57) ABSTRACT

The present invention provides a method for identifying a test compound that binds to a target species. The method includes: incubating at least one test mixture under isothermal denaturing conditions, each test mixture comprising at least one test compound, and at least one target species, wherein the isothermal denaturing conditions are effective to cause at least a portion of the target species to denature to a measurable extent; detecting a denaturation signal of each target species in the presence of the at least one test compound by a change in the diffusion properties of the target molecule using fluorescence correlation spectroscopy; and comparing the denaturation signal of each target species in the presence of at least one test compound with a denaturation signal of the same target species in the absence of the at least one test compound under the same isothermal denaturing conditions.

19 Claims, 6 Drawing Sheets

OTHER PUBLICATIONS

Shosheva et al., Urea folding and stability of gamma–II crystalline, Journal of Photochemistry and Photobiology, 21 (2–3): 183–189 (Dec. 1993). Abstract.*

Sterrer et al., Fluorescence Correlation Spectroscopy (FCS): a highly sensitive method to analyze drug/target interactions, J. Recept. Signal Transduction Res. 17 (1–3), 511–520 (1997). Abstract.*

Thompson et al., Immunoglobulin surface–binding kinetics studies by total internal reflection with fluorescence correlation spectroscopy, Biophys J. 43(1): 103–114 (1983)Abstract.*

Maiti, Sudipta; A study of protein folding with two–photon fluorescence correlation spectroscopy. Biophysical Journal, (1996) vol. 70, No. 2 Part 2, pp. A262.*

Petersen N O, Diffusion and aggregation in biological membranes. Canadian Journal of Biochemistry and Cell Biology, (Nov. 1984) 62 (11) 1158–66. (Abstract).*

Trier et al., Fusion of the binding domain of Raf–1 kinase with green fluorescent protein for activated Ras detection by fluorescence correlation spectroscopy, Pharmazie (Apr. 1999), 54: 4 (263–268). (Abstract).*

S. I. Blaber et al., "Reversible Thermal Denaturation of Human FGF–1 Induced by Low Concentrations of Guanidine Hydrochloride," *Biophysical Journal, 77*, 470–477 (1999).

G. Graziano, et al., "DSC Study of the Thermal Stability of S–Protein and S–Peptide/S–Protein Complexes," *Biochemistry, 35*, 13386–13392 (1996).

S. Maiti et al., "A study of protein folding with two–photon fluorescence correlation spectroscopy," *Biophysical Journal, 70*(2):part 2, A262 (Feb. 17–21, 1996).

L. O. Narhi et al., "Reversibility of Heat–Induced Denaturation of the Recombinant Human Megakaryocyte Growth and Development Factor," *Pharm. Res., 16*, 799–807 (1999).

R. Rigler, "Fluorescence correlations, single molecule detection and large number screening, Applications in biotechnology," *Journal of Biotechnology, 41*, 177–186 (1995).

A. C. Shosheva et al., "Urea unfolding and stability of gamma–II crystalline," *J. Photochem. Photobiol. B: Biol., 21*, 183–189 (1993).

S. Sterrer et al., "Fluorescence Correlation Spectroscopy (FCS): A Highly Sensitive Method to Analyze Drug/Target Interactions," *J. of Receptor & Signal Transduction Research, 17*:(1–3), 511–520 (1997).

N. L. Thompson et al., "Immunoglobulin surface–binding kinetics studied by total internal reflection with fluorescence correlation spectroscopy," *Biophys. J., 43*, 103–114 (1983).

Babu et al., "Ionic–strength–dependent transition of hen egg–white lysozyme at low pH to a compact state and its aggregation on thermal denaturation," *Eur. J. Biochem., 245*:781–789 (1997).

Berland et al., "Two–Photon Fluorescence Correlation Spectroscopy: Method and Application to the Intracellular Environment," *Biophys. J., 68*(2):694–701 (1995).

Berland et al., "Scanning Two–Photon Fluctuation Correlation Spectroscopy: Particle Counting Measurements for Detection of Molecular Aggregation," *Biophys. J., 71*:410–420 (1996).

Brandts, "The Thermodynamics of Protein Denaturation. I. The Denaturation of Chymotrypsinogen," *J. Am. Chem. Soc., 86*:4291–4301 (1964).

Brandts, "The Thermodynamics of Protein Denaturation. II. A Model of Reversible Denaturation and Interpretations Regarding the Stability of Chymotrypsinogen," *J. Am. Chem. Soc., 86*:4301–4314 (1964).

Brandts et al., "The Thermodynamics of Protein Denaturation. III. The Denaturation of Ribonuclease in Water and in Aqueous Urea and Aqueous Ethanol Mixtures," *J. Am. Chem. Soc., 89*(19):4826–4838 (1967).

Chan et al., "Effects of Additives on Heat Denaturation of rhDNase in Solutions," *Pharm. Res., 13*(5):756–761 (1996).

Chen et al., "The Photon Counting Histogram in Fluorescence Fluctuation Spectroscopy," *Biophys. J., 77*(1):553–567 (1999).

Cho et al., "The Binding Site of a Specific Aminoglycoside Binding RNA Molecule," *Biochemistry, 37*(14):4985–4992 (1998).

Douthwaite et al., "Erythromycin Binding is Reduced in Ribosomes with Conformational Alterations in the 23 S rRNA Peptidyl Transferase Loop," *J. Mol. Biol., 232*:725–731 (1993).

Egebjerg et al., "Binding sites of the antibiotics pactamycin and celesticetin on ribosomal RNAs," *Biochimie, 73*:1145–1149 (1991).

Ehlert et al., "Specificities of FemA and FemB for Different Glycine Residues: FemB Cannot Substitute for FemA in Staphylococcal Peptidoglycan Pentaglycine Side Chain Formation," *J. Bacteriol., 179*(23):7573–7576 (1997).

Elson et al., "Concentration Correlation Spectroscopy: A New Biophysical Probe Based on Occupation Number Fluctuations," *Annu. Rev. Biophys. Bioeng., 4*: 311–334 (1975).

Epps et al., "The Constituent Tryptophans and bisANS as Fluorescent Probes of the Active Site and of a Secondary Binding Site of Stromelysin–1 (MMP–3)," *J. Prot. Chem., 17*(7):699–712 (1998).

Ferrer et al., "Partially folded, molten globule and molten coil states of bovine pancreatic trypsin inhibitor," *Structural Biology, 2*(3):211–217 (1995).

Finzel et al., "Structural characterizations of nonpeptidic thiadiazole inhibitors of matrix metalloproteinases reveal the basis for stromelysin selectivity," *Prot. Sci., 7*:2118–2126 (1998).

Foster et al., "Pharmacological Rescue of Mutant p53 Conformation and Function," *Science, 286*(5449):2507–2510 (1999).

Gloss et al., "Urea and Thermal Equilibrium Denaturation Studies on the Dimerization Domain of *Escherichia coli* Trp Repressor," *Biochemistry, 36*(19):5612–5623 (1997).

Handbook of Fluorescent Probes and Research Chemicals, "3.2 Hydrazines and Aromatic Amines for Modifying Aldehydes and Ketones," www.probes.com/handbook/sections/0302.html, 5 pages (page updated Feb. 4, 2000).

He et al., "Comparison of Inactivation and Unfolding of Yeast Alcohol Dehydrogenase During Thermal Denaturation," *Int. J. Biochem. Cell Biol., 29*(7):1021–1028 (1997).

Imai, "Purification and Characterization of a Pyridine Nucleotide Glycohydrolase from Rabbit Spleen," *J. Biochem., 106*(5):928–937 (1989).

Jones et al., "New Fluorescent Assay for Detection and Quantitation of Nanogram Levels of Proteins in Solution," *FASEB J.*, p. A1512, abstract 2954, 2 pages (1996).

Kam et al., "Simple schemes for measuring autocorrelation functions," *Rev. Sci. Instrum., 46*(3):269–277 (1975).

Kettling et al., "Real–time enzyme kinetics monitored by dual–color fluorescence cross–correlation spectroscopy," *Proc. Natl. Acad. Sci. USA, 95*:1416–1420 (1998).

Kotik et al., "Evidence for Temperature–Dependent Conformational Changes in the L–Lactate Dehydrogenase from *Bacillus stearothermophilus,*" *Biochemistry, 31*(34):7787–7795 (1992).

Kurganov et al., "Analysis of differential scanning calorimetry data for proteins: Criteria of validity of one–step mechanism of irreversible protein denaturation," *Biophys. Chem.*, 69:125–135 (1997).

Lavie et al., "Structure of thymidylate kinase reveals the cause behind the limiting step in AZT activation," *Nature Structural Biology*, 4(8):601–604 (1997).

Leviev et al., "A conserved secondary structural motif in 23S rRNA defines the site of interaction of amicetin, a universal inhibitor of peptide bond formation," *EMBO J.*, 13(7):1682–1686 (1994).

Mei et al., "Inhibitors of Protein–RNA Complexation That Target the RNA: Specific Recognition of Human Immunodeficiency Virus Type 1 TAR RNA by Small Organic Molecules," *Biochemistry*, 37(40):14204–14212 (1998).

Merkler et al., "Aggregation and thermo–inactivation of glutamine synthetase from an extreme thermophile, *Bacillus caldolyticus*," *Biochim. Biophys. Acta*, 952:101–114 (1988).

Mildner et al., "The HIV–1 Protease as Enzyme and Substrate: Mutagenesis of Autolysis Sites and Generation of a Stable Mutant with Retained Kinetic Properties," *Biochemistry*, 33(32):9405–9413 (1994).

Moore et al., "Single Molecule Detection Technologies in Miniaturized High Throughput Screening: Fluorescence Correlation Spectroscopy," *J. Biomol. Screening*, 4(6):335–353 (1999).

Moses et al., "Basic Pancreatic Trypsin Inhibitor has Unusual Thermodynamic Stability Parameters," *J. Mol. Biol.*, 170:765–776 (1983).

Payne et al., "Ligand stabilization of cholinesterases," *Biochim. Biophys. Acta*, 999:46–51 (1989).

Petersen et al., "[19] Measurements of Diffusion and Chemical Kinetics by Fluorescence Photobleaching Recovery and Fluorescence Correlation Spectroscopy," *Methods in Enzymol.*, 130: 454–484 (1986).

Poklar et al., "pH and Temperature–Induced Molten Globule–Like Denatured States of Equinatoxin II: A Study by UV–Melting, DSC, Far– and Near–UV CD Spectroscopy, and ANS Fluorescence," *Biochemistry*, 36(47):14345–14352 (1997).

Protasevich et al., "Comparative Study of Monoclonal Immunoglobulin M and Rheumatoid Immunoglobulin M by Differential Scanning Microcalorimetry," *Biochemistry (Moscow)*, 62(8):914–918, Translated from *Biokhimiya*, 62(8):1066–1071 (1997).

Rauer et al., "Fluorescence correlation spectrometry of the interaction kinetics of tetramethylrhodamin –bungarotoxin with *Torpedo californica* acetylcholine receptor," *Biophys. Chem.*, 58:3–12 (1996).

Rosendahl et al., "The antibiotics micrococcin and thiostrepton interact directly with 23S rRNA nucleotides 1067A and 1059A," *Nuc. Acids Res.*, 22(3):357–363 (1994).

Ruvinov et al., "Ligand–mediated Changes in the Tryptophan Synthase Indole Tunnel Probed by Nile Red Fluorescence with Wild Type, Mutant, and Chemically Modified Enzymes," *J. Biol. Chem.*, 270(11):6357–6369 (1995).

Sackett et al., "Nile Red as a Polarity–Sensitive Fluorescent Probe of Hydrophobic Protein Surfaces," *Anal. Biochem.*, 167:228–234 (1987).

Sackett et al., "Hydrophobic Surfaces of Tubulin Probed by Time–resolved and Steady–state Fluorescence of Nile Red," *J. Biol. Chem.*, 265(25):14899–14906 (1990).

Sarver et. al., "Thermodynamic and circular dichroism studies differentiate inhibitor interactions with the stromelysin $S_1$–$S_3$ and $S'_1$–$S'_3$ subsites," *Biochim. Biophys. Acta*, 1434:304–316 (1999).

Sontum et al., "Photon correlation spectroscopy applied to characterisation of denaturation and thermal stability of human albumin," *J. Pharm. Biomed. Anal.*, 16:295–302 (1997).

Spickler et al., "Streptomycin Binds to the Decoding Center of 16 S Ribosomal RNA," *J. Mol. Biol.*, 273:586–599 (1997).

Steinberg et al., "SYPRO Orange and SYPRO Red Protein Gel Stains: One–Step Fluorescent Staining of Denaturing Gels for Detection of Nanogram Levels of Protein," *Anal. Biochem.*, 239:223–237 (1996).

Steinberg et al., "Applications of SYPRO Orange and SYPRO Red Protein Gel Stains," *Anal. Biochem.*, 239:238–245 (1996).

Szeltner et al., "Conformational Stability and Catalytic Activity of HIV–1 Protease Are Both Enhanced at High Salt Concentration," *J. Biol. Chem.*, 271(10):5458–5463 (1996).

Tschierske et al., "Lif, the lysostaphin immunity factor, complements FemB in staphylococcal peptidoglycan interpeptide bridge formation," *FEMS Microbiol. Lett.*, 153:261–264 (1997).

Tuerk et al., "Systematic Evolution of Ligands by Exponential Enrichment: RNA Ligands to Bacteriophage T4 DNA Polymerase," *Science*, 249:505–510 (1990).

Uversky et al., "Use of fluorescence decay times of 8–ANS–protein complexes to study the conformational transitions in proteins which unfold through the molten globule state," *Biophys. Chem.*, 60:79–88 (1996).

Werstuck et al., "Controlling Gene Expression in Living Cells through Small Molecule–RNA Interactions," *Science*, 282:296–298 (1998).

Wong et al., "Specificity of aminoglycoside antibiotics for the A–site of the decoding region of ribosomal RNA," *Chemistry & Biology*, 5:397–406 (1998).

Yamaoka et al., "A pharmacokinetic analysis program (multi) for microcomputer," *J. Pharm. Dyn.*, 4(11):879–885 (1981).

Ibarra–Molero et al., "Thermal versus guandinine–induced unfolding of ubiquitin. An analysis in terms of the contributions from charge–charge interactions to protein stability" *Biochemistry*, 38: 8138–8149 (1999).

Bagshaw et al., "Measurement of Ligand Binding to Proteins," *Spectrophotometry & spectrofluorimetry: a practical approach*, Harris et al., eds., IRL Press, Oxford, UK, pp. 91–113 (1987).

Bell, J.E., "Fluorescence: Solution Studies," *Spectroscopy in Biochemistry*, vol. I, Bell, ed., CRC Press, Boca Raton, Florida, pp. 155–194 (1981).

Brand, et al., "Fluorescence Probes For Structure,"*Ann. Rev. Biochem.*, vol. 41, Snell et al., eds., Annual Reviews Inc., Palo Alto, CA, pp 41:843–868 (1972).

Eigen et al., "Sorting single molecules: Application to diagnostics and evolutionary biotechnology," *Proc. Natl. Acad. Sci. USA*, 91, 5740–5747 (Jun. 1994).

* cited by examiner

US 6,582,907 B1

USE OF FLUORESCENCE CORRELATION SPECTROSCOPY TO IDENTIFY COMPOUNDS THAT BIND TO TARGET SPECIES UNDER ISOTHERMAL DENATURING CONDITIONS

BACKGROUND OF THE INVENTION

One of the major challenges facing the drug discovery process is the identification of small organic ligands that will bind to target species, particularly protein targets. A multitude of new protein targets are being discovered by genomics and bioinformatics efforts. Many of these proteins have no known function or known specific ligands. Thus, the identification of ligands for these targets presents challenges in the screening of large chemical libraries by high throughput screening (HTS), including ultra-high throughput screening (UHTS), methods, particularly from the standpoint of assay development. Hence, there is a need for a straightforward, generally applicable methodology, particularly an HTS assay methodology, that can be used to identify ligands that bind proteins, especially those with unknown functionality.

It is known that the binding of substrates or specific ligands does, in general, alter the intrinsic stability and hence the denaturation profile of a protein. Thus, methods that measure protein denaturation can be used to detect and quantitate ligand-protein interactions.

The denaturation of proteins is accompanied by the progressive loss of their tertiary/quartenary structure and ultimately biological activity. Denaturation can be accomplished by a number of physical and chemical methods that involve changes in temperature, pH, and/or ionic strength, use of chaotropic agents, etc. It can be followed by methods sufficiently sensitive to monitor conformational changes in a protein. Because it is a simple and widely applicable experimental method, thermal denaturation has been used for a variety of purposes, including purifying proteins by selective denaturation of impurities and to study protein structure, folding, and stability. Thermal denaturation curves ((TDC), where the fraction of denatured protein is measured as a function of gradually increasing temperatures) obtained by differential scanning calorimetry (DSC) have been shown to be particularly useful for determining protein stability and making inferences about the tertiary structure. The usefulness of TDC is further enhanced because binding of compounds that are substrates or specific ligands for a given protein changes the intrinsic stability of that protein and, hence, causes a shift in the TDC and the $T_m$ (midpoint temperature) values.

Interpretation of the results of thermal scanning methods depends on the assumption that the denaturation process is a one-step, reversible, and continuous process that is very rapid on the time scale of the temperature scanning rate. However, the denaturation of most proteins under the usual experimental conditions is irreversible. Typically, it is only with small proteins and very mild denaturing agents that denaturation is readily reversible. Thus, DSC may be unable to provide reproducible and readily interpretable binding measurements.

In general, the DSC curves reflect the stability of many different structural domains, some sensitive to the binding of ligands and some not sensitive at all. Furthermore, denaturation may be initiated at many locations within the protein structure. Each of these processes has its own activation energy, which makes it the dominant process only within a narrow temperature range. As a consequence, depending on the scanning rate, the stability of a given domain may or may not be evident in the DSC curve. Furthermore, differential scanning calorimetry may see two or more protein denaturation steps where one would expect only a single transition. Yet another major factor contributing to the greater inextricability of the scanning thermal denaturation methods is that the binding equilibria of both the ligands of interest and of the fluorescent dyes reporting on the structural integrity of the protein are strongly temperature dependent. Thus, both the sensitivity of the method and the stabilizing effect of the ligand under study drift drastically during the experiment.

Therefore, a need exists for a method identifying compounds that bind to target species. Preferably, such a method is amenable to UHTS or HTS, reproducible, and independent of the heating rate.

SUMMARY OF THE INVENTION

The present invention provides methods for identifying compounds that bind to target species (e.g., polypeptides including proteins, and polynucleotides including DNA and RNA). These methods involve the use of isothermal denaturation, preferably in combination with fluoresence detection methods. Significantly, the methods of the present invention involve automated methods suitable for HTS and UHTS. Ideally, the methods of the present invention arc envisioned to be scalable to evaluate 10,000–60,000 compounds or more in a 24 hour period.

Isothermal denaturation of proteins offers an attractive method for the identification of binding ligands. Significantly, in preferred methods, the present invention couples fluorescence techniques with denaturation by isothermal methods to determine alteration of target (e.g., protein) stability by a bound ligand. In particularly preferred embodiments, the denaturation and stabilization or destabilization of target species (e.g., protein targets) by ligands against isothermal denaturation is quantified by changes in fluorescence intensity.

In one preferred embodiment, the present invention provides a method for identifying a test compound that binds to a target species. The method includes: incubating at least one test mixture (preferably, a plurality of test mixtures for high throughput screening) under isothermal denaturing conditions, each test mixture comprising at least one test compound (preferably, at least two test compounds and more preferably, twp to ten test compounds), and at least one target species (preferably, only one target species is in any one test mixture), wherein the isothermal denaturing conditions are effective to cause at least a portion of the target species to denature (e.g., unfold) to a measurable extent; detecting a denaturation signal of each target species in the presence of the at least one test compound by a change in the diffusion properties of the target molecule using fluorescence correlation spectroscopy; and comparing the denaturation signal of each target species in the presence of at least one test compound with a denaturation signal of the same target species in the absence of the at least one test compound under the same isothermal denaturing conditions. Typically and preferably, the methods of the present invention can evaluate at least about 100 test mixtures per day. Preferably, such an evaluation occurs substantially simultaneously.

In the methods described herein, the target species can be a polypeptide (e.g., protein) or a polynucleotide (e.g., DNA or RNA). Preferably, the target species is a protein. The compound can bind to the target species either specifically (e.g., at a specific site or in a specific manner) or unspecifically. The binding can involve a variety of mechanisms, including covalent bonding, ionic bonding, hydrogen bonding, hydrophobic bonding (involving van der Waals forces), for example, or combinations thereof.

DEFINITIONS

In the present invention the following definitions apply:

Isothermal denaturing conditions refers to conditions effective to denature a target molecule at a fixed temperature. It can also involve defined conditions with respect to pH, ionic strength, cation concentration, etc., which are generally held constant for evaluation of various compounds for a given target.

Denaturation signal refers to the signal produced by the target species upon being denatured.

$T_m$ refers to the midpoint of the melting transition of the target as determined by differential scanning calorimetry.

Reporter molecule refers to a separately added molecule such as a fluorescent dye or a covalently bonded reporter group attached to the target.

DETAILED DESCRIPTION OF PREFERRED EMBODIMENTS

Figure 1:
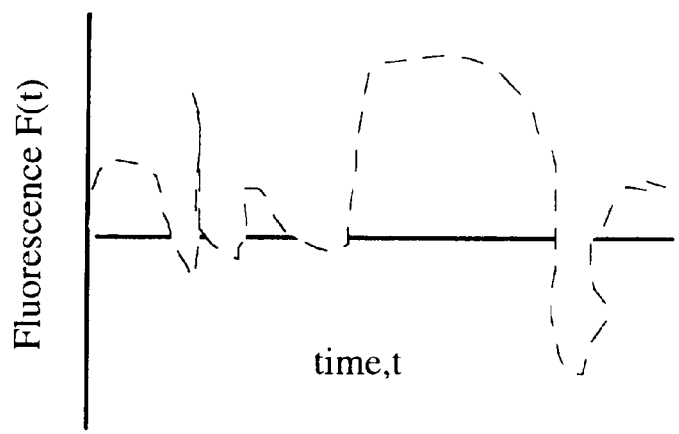
FIG. 1. Fluctuation of fluorescence in a small volume as a function of time.

The present invention is directed to the use of isothermal denaturation. The methodology can be used to screen for ligands to a wide variety of molecules, particularly proteins, including those with unknown function. Significantly, the methods of the present invention eliminate the necessity of ramping temperatures up and down and should allow for much faster assay development and higher throughput in an HTS or UHTS automated environment. The technology should be easily expandable to looking for compounds that bind to RNA, DNA, α-acidic glycoprotein, and serum albumin, for example.

Isothermal denaturation offers an attractive alternative method for monitoring denaturation (e.g., unfolding of a target species) and for the identification of binding ligands. It is amenable to HTS and UHTS. Furthermore, the denaturation process is easily controllable, reproducible, and independent of the heating rate.

The choice of temperature used in isothermal denaturation can be determined by measuring the rate of denaturation of the target species at a series of temperatures (e.g., within a range of about 45° C. to about 75° C.). These measurements may be made, for example, using a fluorescent reporter molecule that binds to and reports conformational changes associated with the unfolding of the target molecule. Preferably, a preliminary DSC scan is run to determine $T_m$ (midpoint temperature) of the target species in appropriate buffers that enhance the stability of the target over a long period of time as would be known to one skilled in the art.

During the binding experiments, all components are maintained at one given temperature (preferably±about 0.2° C.) which is chosen to produce aslow, easily monitored denaturation of the target protein. If the temperature of isothermal denaturation is too low, the kinetics are too slow. Generally, it is desirable to have a detectable amount of denaturing (e.g., unfolding) occur within about 60 minutes or less. If the temperature is too high, the kinetics are so fast that the test compound would not be able to stabilize the denatured target species resulting, for example, in too great an extent of unfolding. Too much unfolding can cause aggregation that could result in precipitation of the target. Furthermore, at too high a temperature, the test compound may not bind at all. Preferably, the desired temperature for isothermal denaturing is equal to the $T_m$ value±about 10° C. of the target species as determined by DSC. More preferably, this temperature is equal to or up to about 10° C. less than the $T_m$ value of the target species.

The target species, preferably together with a suitable reporter molecule able to monitor its denaturation, is incubated in the presence and absence of the test compound. In a preferred embodiment, the concentration of the target species and that of the reporter molecule are of comparable magnitude (preferably, no greater than about 1 $\mu$M), but may require the reporter molecule to be in excess relative to the target molecule, whereas the concentration of the test compound is in at least a 10-fold excess. The percent inhibition cutoff for a "hit" can be set prior to assay implementation, or determined statistically during or after all screening has been performed.

Fluorescence techniques are rapidly becoming the detection methods of choice, particularly for HTS and UHTS. Thus, fluorescence molecules are used as the markers of choice. Coupling fluorescence techniques with denaturation by isothermal methods is attractive because in isothermal denaturation the quantum yield of an extrinsically added reporter molecule is dependent only on changes in protein folding and not on temperature effects. Further, any change in the fluorescence quantum yield measures binding of the reporter molecule to different denatured forms of the target species. Thus, alteration of target stability by a bound ligand should be easily detectable.

In the methods of the present invention, target species denaturation and stabilization or destabilization by ligands against isothermal denaturation is quantified by fluorescence correlation spectroscopy. As taught in Applicants' Assignee's copending application U.S. Ser. No. 09/458,171, filed on even date herewith, isothermal denaturation can be used to determine if known competitive inhibitors/ligands could bind to target species. The present invention demonstrates the utility of fluorescence correlation spectroscopy (FCS) to monitor denaturation of targets isothermally. Such instruments are commercially available from ISS, Inc., Urbana, Ill. and Zeiss Inc., Jena, Germany. One skilled in the art will appreciate that a screening instrument can be built or modified to perform high throughput screening of compounds that stabilize a target under isothermal conditions. Thus, this new technology has significant potential for adaptation to high- and ultrahigh-throughput screening in drug discovery.

Fluorescence correlation spectroscopy (FCS) is a technique that directly measures the spontaneous fluorescence fluctuation of systems in thermodynamic equilibrium. It is an ultrasensitive technique operating at the level of single fluorescent molecules diffusing in and out of the confocal volume created by a focused laser beam. That is, in FCS, a sharply focused laser beam illuminates a femtoliter volume. This volume is so small that it typically hosts only one particle out of the many under analysis at a given moment in time. The single molecules diffusing through the illuminated volume give rise to bursts of fluorescence light quanta. Each individual burst, resulting from a single molecule, can be registered. In a typical FCS instrument, the photons are recorded in a time resolved manner by a highly sensitive single-photon detection device. All signals resulting from the diffusion of a series of molecules through the confocal volume are recorded. The quanta belonging to particular fluorescing molecules are identified using autocorrelation software. The number of molecules in the illuminated volume, as well as their characteristic translational diffusion times, can be determined.

The spontaneous fluorescence fluctuating quantity is the number of observed molecules in a defined unit volume (FIG. 1), and the diffusion coefficient and the kinetic coefficients of the system are two quantities that are generally measured. In particular, FCS detects the time-dependent spontaneous intensity fluctuations in the fluorescence signal which may derive from Brownian motion, flow, and chemical reactions, such as binding.

Analysis of the shape and decay rate of the autocorrelation function, $$G(\tau) = \{<\delta F(\tau) 67\ F(t+\tau)>\}/<F>$$

for the fluctuating signal reveals information about diffusion coefficients, number of molecules, etc., and the $G(\tau)$ curves vary dependent upon molecular diffusion weights. Definitions of the symbols in the above equation are: $\tau$ represents the correlation time constant; $<F>$ the average total fluorescence; $F(\tau)$ and $F(t+\tau)$ are the fluorescence values measured during the correlation time-constant and at time t plus the correlation time-constant.

Lastly $G(\tau)$ extrapolated to zero time, i.e., the $G(0)$ value, represents the number of molecules in the experimental volume. See, for example, Kam et al., *Rev. Sci. Instrum.*, 46, 269–277 (1975); and Rauer et al., *Biophys. Chem.*, 3–12 (1996). For the equipment used in the studies of the present invention, division of the constant value 0.076 by the $G(0)$ value yields the number of molecules. This constant derives from the volume swept out by the two-photon laser beam defined by, for example, a Gaussian-Lorentzian equation (see the Data Analyses section below) and was experimentally determined.

Figure 2:
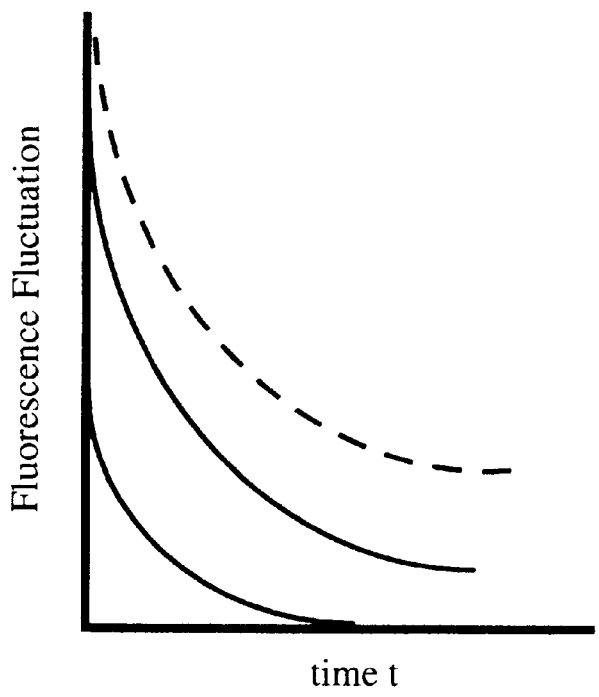
FIG. 2. Fluorescence fluctuations correlated for a given molecular species.

A schematic representation of autocorrelated functions of $G(\tau)$ versus time where, for example, each curve represents different concentrations of a given molecule, a different conformation of the molecule, or some other physical explanation, is shown in FIG. 2.

The observed fluctuations obey Poisson statistics with the amplitude of the average fluctuation being proportional to the square root of N, the number of molecules being observed. In principle, FCS can measure single molecules and the kinetics of the time scale may extend from hundreds of nanoseconds to seconds, with low nanomolar concentrations capable of being detected in an observed volume of 0.1 femtoliter (fL) to 1.0 fL.

The present invention demonstrates that FCS can be used to measure thermal denaturation of target species (e.g., proteins) and determine if known competitive inhibitors/ligands could stabilize these molecules. The results are comparable to those obtained by other methods. The agreement of the denaturation kinetics from three different detection methods confirms that the same unfolding processes are being measured using the methods of the present invention. Since it is relatively easy to label covalently the target molecule without any subsequent concern about how to measure the fluorescence, as opposed to, for example, polarization, intensity, lifetime, etc., an FCS instrument with micro-titer plate capability offers a powerful method for quickly screening large chemical libraries to identify potential drug-leads. Alternatively, one skilled in the art can use the same fluorescent dyes in the same manner as described above for isothermal denaturation.

In order to be able to work at low target concentrations with isothermal denaturation using FCS, one typically and preferably, uses no greater than about 50 nM of the reporter molecule. With isothermal denaturation by FCS it is desirable when using extrinsic but not covalent reporter molecules, that the fluorescence of the extrinsically added dyes bound to denatured target should be at least 2-fold greater than to native target. For proteins, this is typically accompanied by the exposure of the hydrophobic regions of the protein. The reporter molecules should also preferably have low affinity for the native target. That is, the fluorescence of the native target/reporter molecule complex is linear over a wide concentration range or, preferably, does not bind to the native target at all so that it does not become a ligand itself. Finally, since compound libraries generally contain numerous compounds that absorb and/or fluoresce between about 300 nanometers (nm) and about 400 nm, the reporter molecule should preferably have excitation and emission in the visible region where few compounds interfere, e.g., excitation at about 488 nm and emission at about 515 nm.

Such reporter molecules (e.g., fluorescent dyes) are commercially available from sources such as Molecular Probes (Eugene, Oreg.) and fluoresce brightly when bound to hydrophobic regions of the target molecule. These include SYPRO Orange, SYPRO Red, Nano Orange, Nile Red, 1-anilinonaphthalene-8-sulfonic acid (1,8-ANS), and dapoxylbutylsulfonamide (DBS) as well as other dapoxyl analogs. Nano Orange fluorescence provides an ultrasensitive dye with a linear fluorescence range for quantification of proteins in solution of about 10 nanograms/milliliter (ng/mL) to about 10 micrograms/milliliter ($\mu$g/mL) with a very low background fluorescence. SYPRO Orange and SYPRO Red are used for gel staining with sensitivity as good as silver staining. The basis for the increase in fluorescence of the dyes with protein denaturation is their binding to newly exposed hydrophobic sites. 1,8-ANS has been used extensively for many years to monitor the unfolding of proteins; however, its quantum yield when bound to the denatured protein is much lower than those of the dyes discussed above and, thus, would require the use of large quantities of protein and reporter molecule in the assays. DBS is a relatively new, solvatochromic dye whose fluorescence emission may shift as much as 100 nm upon changing the environment. Due to its lower excitation and emission wavelengths, however, it is less desirable than Nano Orange, SYPRO Orange, or SYPRO Red for HTS.

Any fluorescent reporter molecule whose emission intensity increases or decreases when bound to a desired target species can be used for isothermal denaturation. The affinity of a fluorescent reporter molecule toward a target species can be determined by measuring the fluorescence of a given concentration of the reporter molecule in the presence of increasing concentrations of the denatured target species and the native target species. Knowing the affinity then allows one to optimize the concentration of the fluorescent reporter molecule relative to the target species.

In addition to, or instead of, using noncovalent fluorescent reporter molecules that are added to a mixture of the test compound and target species, one may use target species labeled covalently with a pair of fluorophores, one of which quenches the fluorescence of the other. Because unfolding of the target species changes the intermolecular distances between the two fluorophores, the denaturation is accompanied by changes in fluorescence. By labeling the same target species at specific sites, the denaturation at different structural regions can be monitored.

For target species that have a relatively high denaturation temperature, the experiments can be performed in the presence of a chaotrope, such as urea, guanidine hydrochloride, organic solvents, or any other reagents that promote protein denaturation without unduly interfering with binding of the reporter molecule with the target species.

The exact experimental conditions for denaturation of each target molecule will vary. One skilled in the art can make appropriate decisions and/or experimentally determine appropriate buffer systems (pH, ionic strength, ionic co-factors, etc.). For example, the isolectric point (pI) of a protein molecule would help determine what pH would be useful in these studies.

In practice, the methods of the present invention can be carried out in a multi-reservoir sample holder, such as a microtiter plate. Typically, all components but the target species are added and the multi-reservoir sample holder is held at the appropriate temperature for a period of time. After thermal equilibrium is reached, the sample holder is preferably transferred to a station where the target species is added to all reservoirs, preferably simultaneously. The multi-reservoir sample holder is typically sealed prior to addition of any components. For example, a microtiter plate can include a covering that is made of a plastic sheeting which seals the plate but is scored in such a way that a microtiter tip easily penetrates it but that it re-closes after tip removal. After introduction of the target species, the sample holder is either transferred immediately to an appropriate detector for reading the denaturation signal or to an incubator for holding until detection is desired. All steps can be performed either manually or by robot as desired.

Using the methods of the present invention, the denaturation of S. aureus FemB and HIV-1 protease, the latter in the absence and presence of a known inhibitor, were evaluated. The measurement of denaturation was based on a change in the diffusion coefficient of the protein as monitored by FCS.

The enzyme HIV-1 protease exists as a dimer. These data are by far the most intriguing in that the apparent diffusion coefficient increases and then decreases. This observation can be interpreted as first the dimer dissociating into monomers with possibly some concurrent denaturation followed by denaturation and/or aggregation. The calculated diffusion coefficients are what would be expected for a protein of this size that dedimerizes and/or then denatures. More importantly, the concept of stabilizing a denatured protein was demonstrated using the competitive HIV-1 protease inhibitor PNU-140690, which has the following structure.

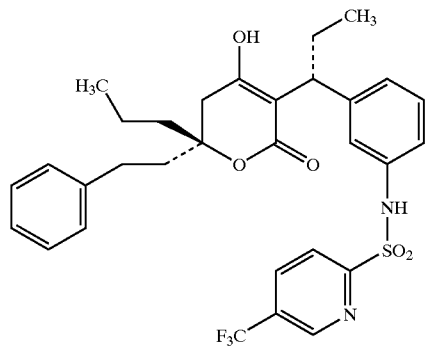

These results show that, indeed, protein denaturation and stabilization by ligands against isothermal denaturation can be quantified by FCS and that this new technology has significant potential for adaptation to ultra high-throughput screening.

The method of the present invention can also be used with RNA and DNA as a target species. Fluorescent dyes can be used to covalently label and monitor the transition from an ordered to a disordered RNA structure include fluorescein, BODIPY™ TMR, Oregon Green, etc. After isolation of the expressed RNA molecule, the 3'-ribose is oxidized and labeled according to published protocols (e. g., http://www.probes. com/handbook/sections/0302.html). Examples of RNA molecules that can be used to demonstrate this approach include: 1) HIV-1 tar 47–86 (Mei et al., Biochemistry, 37, 14204–14212 (1998)); 2) RNA aptamer J6fl (Cho et al., Biochemistry, 37, 4985–4992 (1998)); and 3) A-site of 16s rRNA (Wong et al., Chemistry and Biology, 5, 397–406 (1998)). Ligands known to bind to these respective RNA molecules are: 1) Neomycin, other aminoglycoside antibiotics, and other compounds (Mei et al., Biochemistry, 37, 14204–14212 (1998)); 2) tobramycin ((Cho et al., Biochemistry 37, 4985–4992 (1998)); and 3) Kanamycin and other aminoglycides (Wong et al., Chemistry and Biology, 5, 397–406 (1998)).

Just as known ligands for proteinaceous targets stabilize their structures under isothermal conditions, these known ligands stabilize their cognate RNA molecules under similar conditions. Similarly, as for protein targets, a large collection of compounds can be tested in high-throughput screening to determine whether any might bind to, and stabilize, these nucleic acid structures under isothermal denaturation conditions. These compounds can be tested singly or as combinations of several compounds.

Having generally described the invention, the same will be more readily understood by reference to the following examples, which are provided by way of illustration and are not intended as limiting.

EXAMPLES

I. Materials

A. Reagents

Oregon Green™ Iodoacetamide, dapoxyl butylsulfonamide, and fluorescein isothiocyanate (FITC) were purchased from Molecular Probes, Eugene, Oreg. Tris-HCl, sodium carbonate, dithiothreitol, mono- and disodium phosphate, β-mercaptoethanol, sodium acetate, glycerol, and sodium chloride were purchased from Sigma-Aldrich, St. Louis, Mo. Ethylene glycol and acetic acid were obtained from Mallinckrodt Laboratory Chemicals, A Division of Mallinckrodt Baker, Inc., Phillipsburg, N.J. Slide-A-Lyzer™ (2,000 MWCO) were purchased from Pierce Chemical, Rockford, Ill. Bio-Gel P-6 Desalting Gel™ spin columns were purchased from BioRad Life Science Research, Hercules, Calif. Micron microconcentrators (10,000 MWCO, $\leq$500 µL) were obtained from Amicon Millipore Corp., Bedford, Mass. The composition of the buffers used in these studies were: for *S. aureus* FemB, 50 mM $NaHCO_3$, 1 mM DTT, pH 9.0.

B. Equipment

Figure 3:
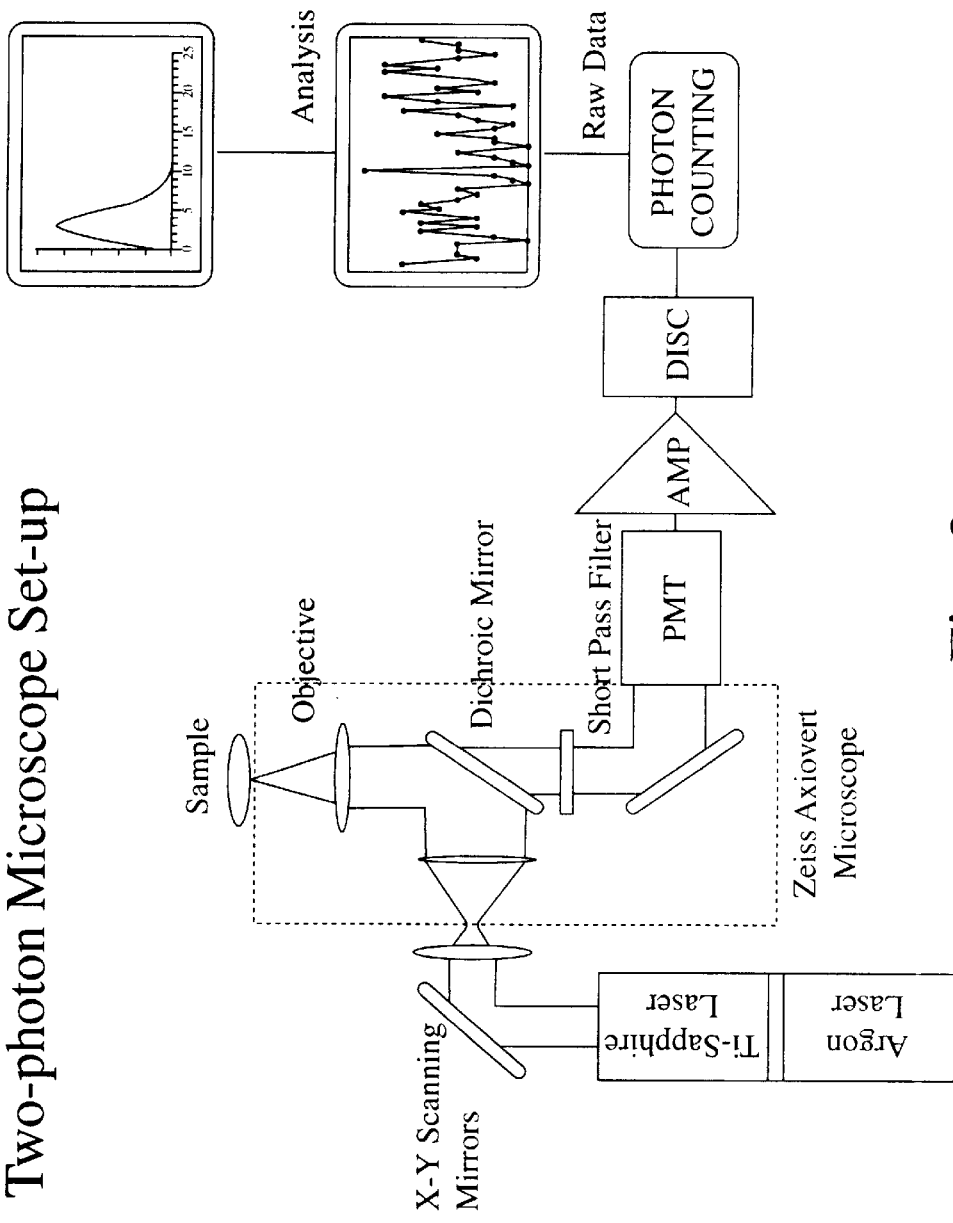
FIG. 3. Schematic of a two-photon FCS instrument.

Fluorescence Correlation Spectroscopy. The fluorescence correlation spectroscopy equipment was built by personnel in the Laboratory of Fluorescence Dynamics (LFD) under the direction of Dr. Enrico Gratton at the University of Illinois (Berland et al., *Biophysical Journal*, 68, 694–701 (1995); Chen et al., *Biophysical Journal*, 77, 553–567 (1999)). A schematic is shown in FIG. 3. It consisted of a Zeiss axiovert microscope, argon (not shown) and titanium-sapphire lasers in series, a photomultiplier tube (PMT) or an avalanche photodiode (APD) as detectors, an autocorrelator and computer with an autocorrelation card. Similar results can be obtained with commercially available instruments such as those sold by ISS, Inc., Urbana, Ill. and by Zeiss Inc., Jena, Germany. The parameters generated by the instrument, especially for the ISS FCS instrument, are the same as those obtained from the instrument used at the LFD of the University of Illinois.

Differential Scanning Calorimetry. Differential scanning calorimetry experiments were performed using an MC-2 ultra-sensitive differential scanning calorimeter from Microcal, Inc., Northampton, Mass.

II. Methods

A. Differential Scanning Calorimetry

Baselines were collected for each enzyme with buffer in both the sample and reference cells (cell volume was 1.2 mL) using a scan rate of 1° C./minute from 25° C. to 90° C. The DSC was cycled through this procedure twice before collecting data for an enzyme to establish a thermal history. Buffer was then removed from the sample cell and enzyme at approximately 1–2 mg/mL was placed in the cell. DSC data were collected for the enzyme from 25° C. to 90° C. at a scan rate of 1° C./minute. The calorimeter was cycled back to 25° C. and protein solution was rescanned to 90° C. Reference baselines were subtracted from sample DSC data. All solutions were degassed prior to DSC collections. The DSC Y-axis was calibrated using known electrical heat pulses. Temperature calibration was performed using n-octadecane and n-hexatriacontane standards which melt at 28.2° C. and 75.9° C., respectively.

B. Labeling of Proteins

*S. aureus* FemB. The protein, *S. aureus* FemB with a molecular size of 50,804 daltons (Ehlert et al., *J. Bacteriol.*, 179, 7573–7576 (1997) and Tschierske et al., *FEMS Microbiol. Lett.*, 153, 261–264 (1997)) was dissolved in 50 mM carbonate buffer, pH 9.0, plus 1 mM dithiothreitol forming a solution of 2.2 mg/mL (43 µM). FITC (100 mg) was dissolved in 100% dimethylsulfoxide (DMSO) at 50 mM and an aliquot diluted to 5 mM in DMSO. The protein was diluted in the same buffer to 20 µM in two 200 µL aliquots and 0.8 µL of 5 mM FITC was added. The reactions were allowed to proceed on ice for 60 minutes. During this time eight BioGel P-6 columns were equilibrated with the $NaHCO_3$/DTT buffer following the manufacturers suggested protocol, spinning at 3000×g for 2 minutes at 4° C. A portion of the reaction mixture (100 µL) was added to four P-6 columns and material was collected. The effluent was collected and the process was repeated. These second eluants were combined and concentrated in the Amicon concentrator using a filter with a 10K micron size cut-off limit with one buffer wash. The retentate was collected and divided into three equal volume aliquots (10.5 µM). One aliquot was evaluated by HPLC analysis and determined that no free, unreacted FITC remained. This material was used in the FCS studies below.

HIV-1 Protease. HIV-1 Protease was extensively dialyzed against 0.1 M sodium phosphate, 0.05% $NaN_3$, pH 6.5, at 5° C., using a Pierce Slide-A-Lyzer™ (2,000 MWCO). The protease concentration was approximately 1 mg/mL. There was a slight turbidity after dialysis. Protease recovery was assumed to be 100% (53 nanomoles in 1.1 mL).

A freshly prepared solution of Oregon Green™ Iodoacetamide (Molecular Probes Inc., Cat. No. O-6010; approximately 10 mM in DMSO) was added at zero and 5 hours of incubation to achieve at each time a 3-fold molar ratio of Oregon Green™ to protease. At approximately 8 hours another addition of a 4-fold molar excess was made. After each addition the solution was gently but thoroughly mixed. Incubations were without agitation at 5° C. and continued for 16 hours after the last addition.

The Oregon Green™/Protease reaction mixture had a significant yellow precipitate and this precipitate was solubilized by the addition of a small volume of glacial acetic acid. The resulting clear solution was chromatographed over a Bio-Gel P-6 Desalting Gel™ column (0.9 cm×25 cm) using 50% volume/volume (v/v) glacial acetic acid/distilled-water as the eluant. The 2.3 mL of yellow solution eluting with the solvent front was retained as the Oregon Green™ conjugated HIV-1 Protease. This was concentrated to 0.9 mL using a Pall Filtron Omega Cell™ (3,000 MWCO), available from Pall Corp., Port Washington, N.Y., at 5° C. using 45 psi helium. Five mL of cold buffer (0.1 M acetic acid, 10% v/v glycerol, 5% v/v ethylene glycol, 1 mM dithiothreitol, pH 5.0) was added to the protease solution at 5° C. with rapid mixing and the pH was adjusted within the range of 4.1 to 4.7. The final pH of the solution after equilibration was 4.8.

The solution of conjugated protease was 0.2 micron filtered and evaluated for Oregon Green™ concentration by extinction and for protease concentration by amino acid analysis. Spectrophotometric results determined an Oregon Green™ concentration of 1.94 µM. Amino acid analysis established a protease concentration of 18 micrograms/mL which is 0.95 µM assuming a protease formula weight of 19 kD. Also, the concentration of carboxy-methyl-cysteine (a hydrolysis product of the iodoacetamide conjugated cysteine) was estimated at 1.8 µM. All of these results are consistent with a nearly complete reaction between the accessible sulfhydryl of HIV-1 Protease and the Oregon Green™ Iodoacetamide.

C. FCS Isothermal Studies

Microfuge tubes containing 1.5 mL buffer were placed in a pre-equilibrated 48° C. water bath and the temperature was monitored with a telethermometer. When temperature was attained, protein was added to 100 nM in the appropriate buffer, rapidly mixed, and an aliquot was removed at various time points. For *S. aureus* FemB, HIV-1 protease, or for HIV-1 protease co-incubated with PNU-140690 (structure listed above), time points were taken from 0 to 60 minutes.

This material was diluted to 10 nM in a 2.0 mL teflon chamber already located on the microscope stage containing the same buffer at room temperature. The solution was thoroughly mixed and data were acquired immediately for two minutes. Data were acquired for 2 to 5 minutes at a scan rate of 10 Khz or 20 Khz. These data were then binned using P-Wave software and immediately assessed using N-Fit software. Binning combines the fluorescence measurements from contiguous time-periods. P-Wave and N-fit were software programs employed at the LFD. Data which looked as if an experimental error had occurred were repeated, otherwise the data were compressed for future analysis. The ISS FCS instrument performs similar analyses in a proprietary computational package that comes with the instrument.

D. Data Analyses

The autocorrelated data were analyzed with a nonlinear least squares (NLLSF) fitting program based on that disclosed in Yamaoka et. al., *J. Pharmacobio Dyn.*, 4, 8–15 (1981). The equation used for analysis was for a single molecular species:

$$G(\tau) = \frac{G(0)/(1 + 1.142 * Diff - Coeffic * binned - time)}{\sqrt{(1 + 1.487 * Diff - Coeffic * binned - time)}} + Background.$$

The constants 1.487 and 1.142 derive from measuring the volume encompassed by the laser beam for this specific instrument and had been determined experimentally.

In these experiments, since both native and denatured proteins exist, the calculated results represent an average value for the amount of material in the two states. Data analyzed with a two species model for *S. aureus* FemB and for HIV-1 protease demonstrated that the G(0) and diffusion coefficient values obtained for the native and denatured species from this analysis were identical to those calculated by the single species analysis for the completely native or completely denatured proteins. These results, plus the fact that changes in the apparent diffusion coefficient values were being monitored, justifies a single species analysis. The data were analyzed with weighting values of either zero or single inverse weighting. The former places equivalent value on all data points; the latter gives greater weight to those points that lie on the curvature of the theoretical fit. Determination of which weighting factor is more appropriate is ascertained by a visual inspection of the theoretical fit in combination with the residuals generated and other statistical analyses.

III. Results

A. Differential Calorimetry Studies

Figure 4:
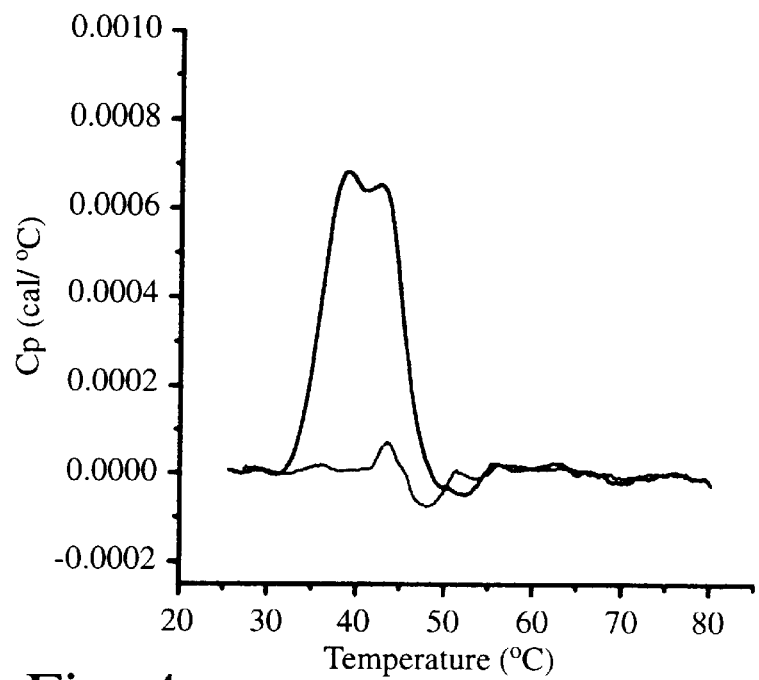
FIG. 4. DSC for S. aureus FemB.

The concentration of FemB was 2.2 mg/mL and the DSC experiment was performed with the unlabeled protein in 50 mM NaHCO$_3$, 1 mM DTT, pH 9.0 (FIG. 4). This protein exhibited two transition temperatures, one at 39.1° C. and the other at 42.2° C. (solid line). FemB also exhibited irreversible denaturation when cooled to 25° C. and rescanned (dotted line).

Figure 5:
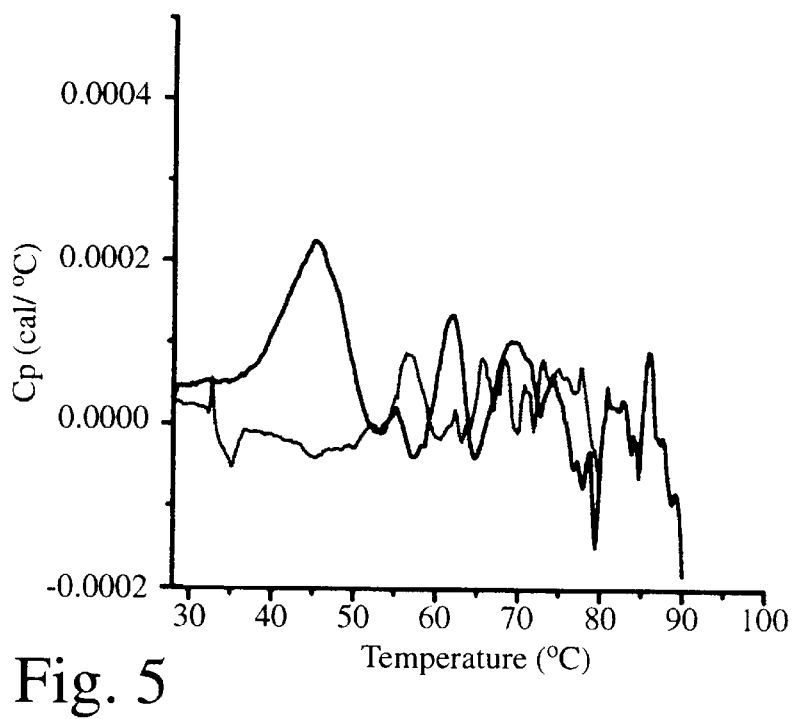
FIG. 5. DSC for HIV-1 protease.

The HIV protease (1.7 mg/mL) study was performed in an identical manner but using the buffer 0.1 M HOAc, 0.2 M NaCl, 10% glycerol (v/v) and 5% ethylene glycol (v/v). In the first scan, the protein showed a $T_m$ of 45.6° C. (FIG. 5, solid line). Significant noise was observed after the transition because precipitate formed upon unfolding. This solution was cooled to 25° C. and upon rescanning, yielded the curve shown by the dotted line, which had no transition at 45° C. Significant noise throughout the scan was due to precipitate in the cell.

B. Fluorescence Correlation Spectroscopy Studies

Figure 6:
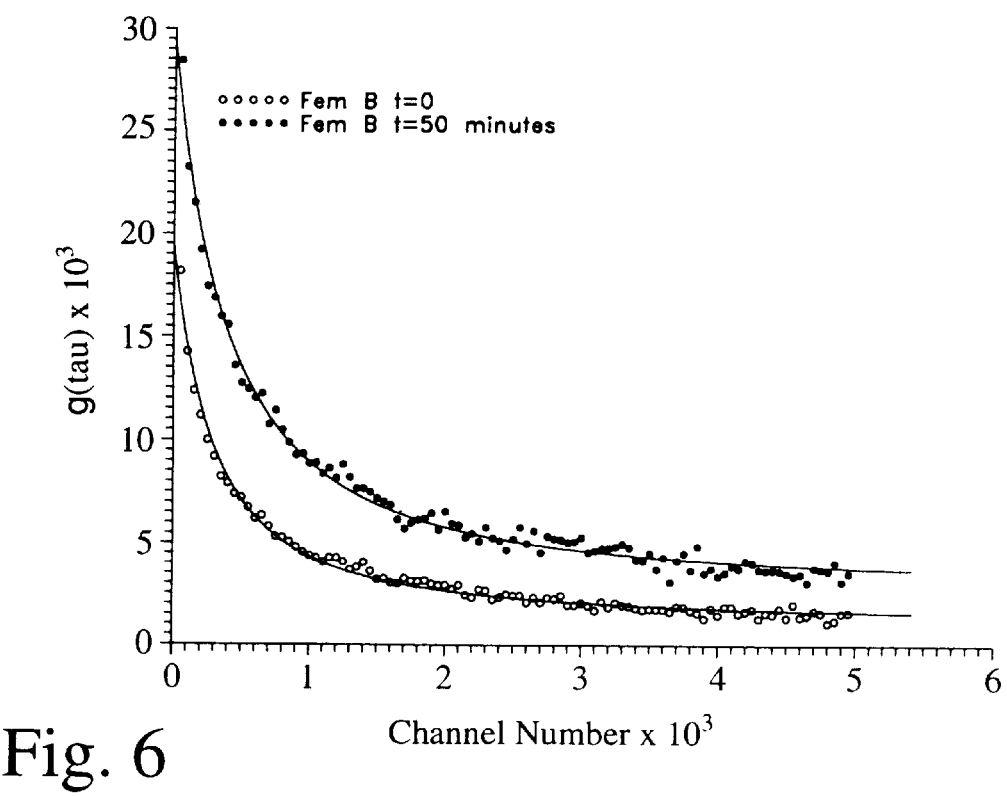
FIG. 6. FemB autocorrelation curves at 45° C. for 0 and 50 minutes.

From the DSC scans it was concluded that a single temperature of approximately 48° C. would be practical for performing isothermal denaturation studies. Consequently a water bath was equilibrated to that temperature and the buffers were equilibrated as described above. The two proteins which had been extrinsically labeled, *S. aureus* FemB and HIV-1 protease, were tested first. Two representative autocorrelation curves analyzed by NLLSF with an inverse weighting of the data points for *S. aureus* FemB are shown in FIG. 6.

The time-points shown are for protein incubated at 48° C. for 0 and 50 minutes. The solid line represents the theoretical fit using the equation defined above. The analyses yield the calculated values for the apparent G(0) and diffusion coefficient values. Two obvious conclusions are that the fit for the 0 minute time point is much better than the one at 50 minutes. Since only one species is present for the former the apparent values arc "averaged" for one species. The 50 minute time point represents the averaging of not only the native and denatured species but also various size aggregates that formed because the temperature utilized was approximately 6° C. greater than its $T_m$ value. Nevertheless the fits were quite good.

Figure 7:
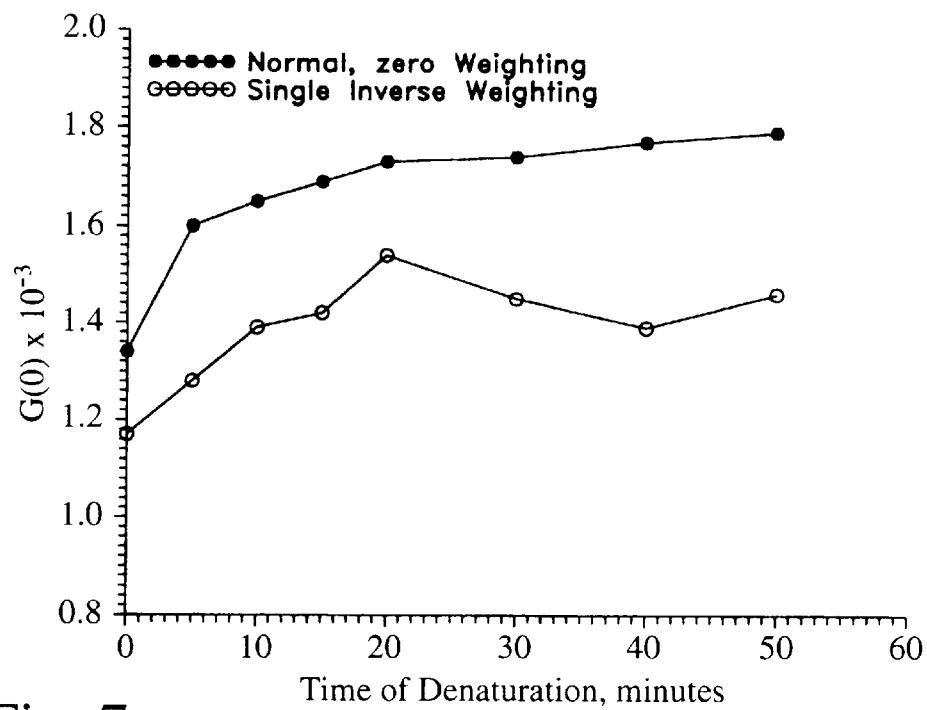
FIG. 7. Change in the calculated G(0) value as a function of FemB denaturation time at 45° C.

The analyses were performed for all of the time points. A plot of the apparent diffusion coefficient versus time at 48° C. is shown in FIG. 7. The two curves represent data generated with either zero or single inverse weighting. In either case, a significant time-dependent change in the apparent diffusion coefficient was observed. This was most pronounced using the single inverse weighting.

These results demonstrate that changes in protein conformations can be monitored by FCS. However, it was not known if a ligand would stabilize a protein and if that stabilization could be monitored by this technique. To test this concept HIV-1 protease and a known, highly potent competitive inhibitor of this enzyme, PNU-140690, were employed. Data were analyzed with single inverse weighting (wt). Two representative curves are shown in FIG. 8.

Figure 8A:
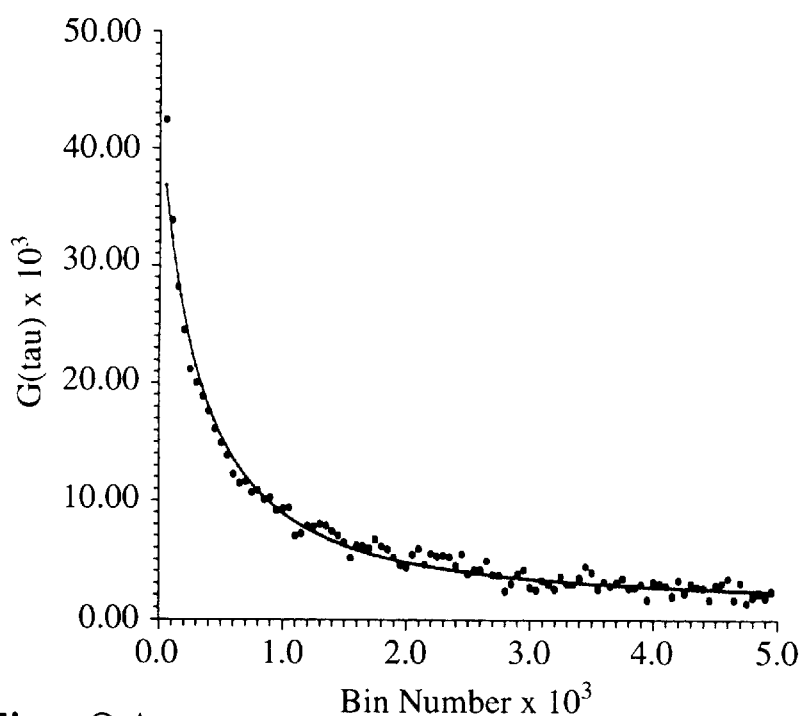
FIG. 8. Autocorrelation curves of HIV-1 Protease +/−PNU-A at 48° C. for 20 minutes (8A) and 24 minutes (8B). A: unimolecular model; diffusion coefficient=1.63× $10^{-6}$±0.11× $10^{-6}$; G(0)=41.3× $10^{-3}$±1.78× $10^{-3}$. B: uninmolecular model; diffusion coefficient=1.33× $10^{-6}$±0.09× $10^{-6}$; G(0) 292× $10^{-3}$±11.7× $10^{-3}$.
Figure 8B:
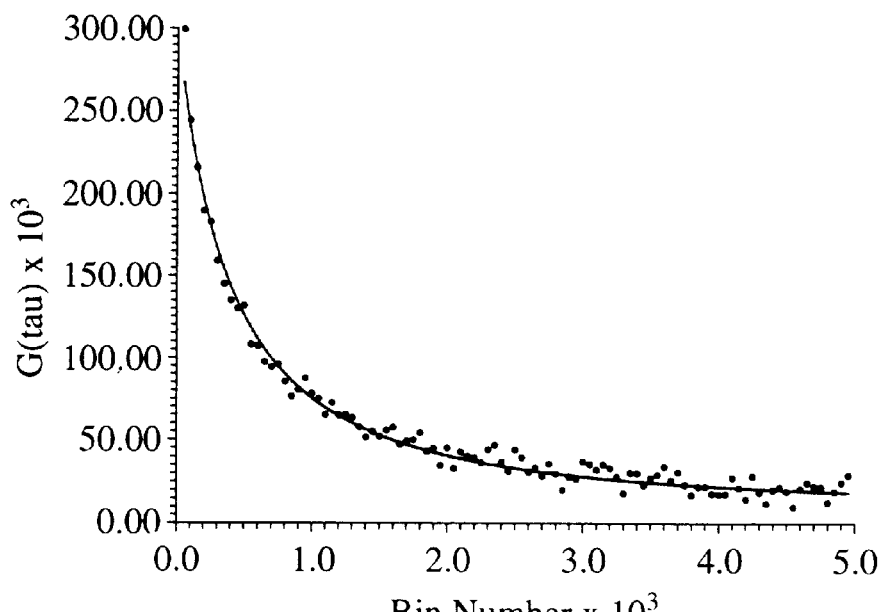

Data for HIV-1 protease at 48° C. for 20 minutes is shown in the top curve and that for the enzyme incubated with PNU-140690 at 48° C. for 24 minutes is shown in the bottom curve of FIG. 8. Both were analyzed with single inverse weighting. These are representative data for the other time points taken with this protein.

Figure 9:
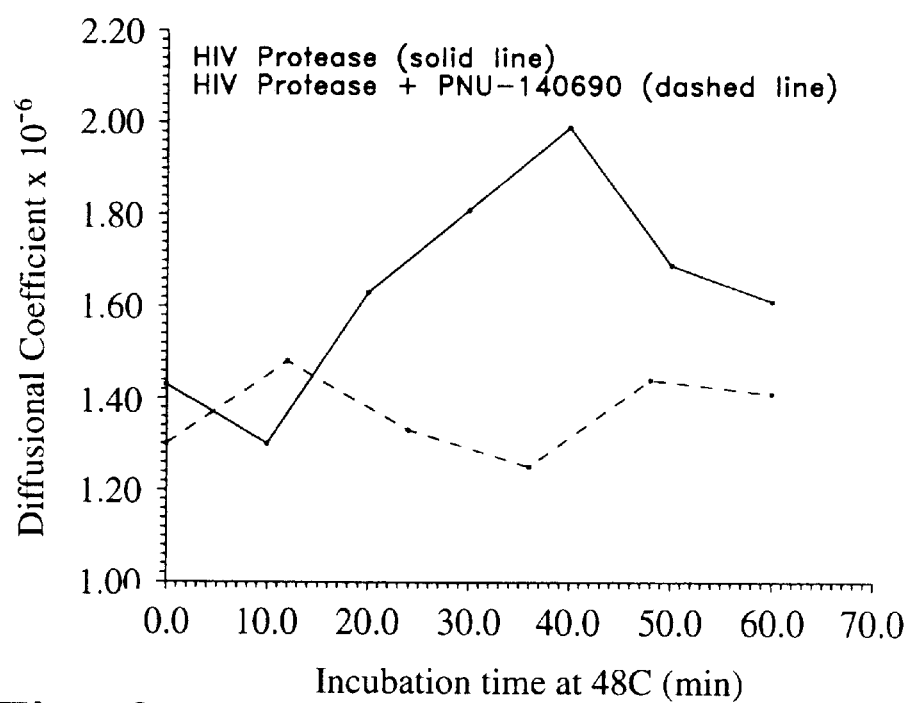
FIG. 9. Time-dependency of the change in the calculated G(0) value of HIV-1 protease in the presence and absence of a test compound at 48° C.

A plot showing the change in apparent diffusion coefficient values at 48° C. for HIV-1 protease with and without PNU-140690 as a function of time is shown in FIG. 9. The competitive inhibitor clearly stabilizes the enzyme with a measurable difference at multiple time points. This result demonstrates the ability to detect small organic molecules that can affect the degree to which a protein changes its conformation in isothermal denaturing conditions.

It will be clear that the invention may be practiced otherwise than as particularly described in the foregoing description and examples. Numerous modifications and variations of the present invention are possible in light of the above teachings and, therefore, are within the scope of the invention. The entire disclosure of all publications, patents, and patent applications cited herein are hereby incorporated by reference.

What is claimed is:

1. A screening method for identifying a test compound that binds to a target species, the method comprising:
   incubating at least one test mixture under isothermal denaturing conditions, each test mixture comprising at least one test compound, at least one reporter molecule, and at least one target species, wherein the isothermal denaturing conditions are effective to cause at least a portion of the target species to denature to a measurable extent;
   detecting a denaturation signal of each target species in the presence of the at least one test compound by monitoring the diffusion properties of the target molecule using fluorescence correlation spectroscopy; and
   comparing the denaturation signal of each target species in the presence of at least one test compound with a denaturation signal of the same target species in the absence of the at least one test compound under the same isothermal denaturing conditions.

2. The method of claim 1 wherein the target species is a polypeptide or a polynucleotide.

3. The method of claim 2 wherein the target species is a protein.

4. The method of claim 1 wherein the compound binds specifically to the target species.

5. The method of claim 1 wherein the compound binds to the target species through hydrophobic, covalent, ionic, or hydrogen bonding interactions.

6. The method of claim 1 wherein the isothermal denaturation conditions comprise a temperature equal to or about 10° C. more or less than the $T_m$ value of the target species as determined by differential scanning calorimetry.

7. The method of claim 6 wherein the isothermal denaturation conditions comprise a temperature equal to or up to about 10° C. less than the $T_m$ value of the target species as determined by differential scanning calorimetry.

8. The method of claim 1 wherein the concentrations of the target species and the reporter molecule are of comparable magnitude.

9. The method of claim 8 wherein the concentration of the at least one test compound is in at least a 10-fold excess relative to the concentration of the at least one target species.

10. The method of claim 1 wherein each test mixture includes one target species.

11. The method of claim 1 wherein each test mixture includes at least two test compounds.

12. The method of claim 11 wherein each test mixture includes two to ten test compounds.

13. A high throughput screening method for identifying a test compound that binds to a target species, the method comprising:

incubating a plurality of test mixtures under isothermal denaturing conditions, each test mixture comprising at least one test compound, at least one reporter molecule, and at least one target species, wherein the isothermal denaturing conditions are effective to cause at least a portion of the target species to denature to a measurable extent;

detecting a denaturation signal of each target species in the presence of the at least one test compound by monitoring the diffusion properties of the target molecule using fluorescence correlation spectroscopy; and comparing the denaturation signal of each target species in the presence of at least one test compound with a denaturation signal of the same target species in the absence of the at least one test compound under the same isothermal denaturing conditions.

14. The method of claim 13 wherein the isothermal denaturation conditions comprise a temperature equal to or about 10° C. more or less than the $T_m$ value of the target species as determined by differential scanning calorimetry.

15. The method of claim 14 wherein the isothermal denaturation conditions comprise a temperature equal to or up to about 10° C. less than the $T_m$ value of the target species as determined by differential scanning calorimetry.

16. The method of claim 15 wherein each test mixture includes one target species.

17. The method of claim 15 wherein each test mixture includes at least two test compounds.

18. The method of claim 17 wherein each test mixture includes two to ten test compounds.

19. A high throughput screening method for identifying a test compound that binds to a protein, the method comprising:

incubating a plurality of test mixtures under isothermal denaturing conditions, each test mixture comprising at least one test compound, at least one reporter molecule, and at least one protein, wherein the isothermal denaturing conditions are effective to cause at least a portion of the protein to denature to a measurable extent;

detecting a denaturation signal of each protein in the presence of the at least one test compound by monitoring the difflusion properties of the target molecule using fluorescence correlation spectroscopy; and comparing the denaturation signal of each protein in the presence of at least one test compound with a denaturation signal of the same protein in the absence of the at least one test compound under the same isothermal denaturing conditions.

* * * * *

UNITED STATES PATENT AND TRADEMARK OFFICE
CERTIFICATE OF CORRECTION

PATENT NO. : 6,582,907 B1
DATED : June 24, 2003
INVENTOR(S) : Epps et al.

It is certified that error appears in the above-identified patent and that said Letters Patent is hereby corrected as shown below:

Column 2,
Line 47, please delete "twp" and insert -- two --.

Column 4,
Line 13, please delete "preferably±about" and insert -- preferably ± about --.
Line 14, please delete "aslow" and insert -- a slow --.
Line 26, please delete "value±about" and insert -- value ± about --.

Column 5,
Line 49, please insert -- *58* -- after "*Biophys. Chem.,*".

Column 9,
Line 6, please delete "≦" and insert -- ≤ --.

Column 12,
Line 10, please delete "arc" and insert -- are --.

Signed and Sealed this

Thirteenth Day of January, 2004

JON W. DUDAS
*Acting Director of the United States Patent and Trademark Office*